US008889739B2

(12) United States Patent
Mozaffarian et al.

(10) Patent No.: US 8,889,739 B2
(45) Date of Patent: Nov. 18, 2014

(54) USE OF TRANS-PALMITOLEATE IN IDENTIFYING AND TREATING METABOLIC DISEASE

(75) Inventors: Dariush Mozaffarian, Boston, MA (US); Haiming Cao, Bethesda, MD (US); Gokhan S. Hotamisligil, Wellesley, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 13/809,181

(22) PCT Filed: Jul. 11, 2011

(86) PCT No.: PCT/US2011/043517
§ 371 (c)(1),
(2), (4) Date: Jan. 9, 2013

(87) PCT Pub. No.: WO2012/006612
PCT Pub. Date: Jan. 12, 2012

(65) Prior Publication Data
US 2013/0267599 A1 Oct. 10, 2013

Related U.S. Application Data

(60) Provisional application No. 61/362,838, filed on Jul. 9, 2010, provisional application No. 61/373,956, filed on Aug. 16, 2010.

(51) Int. Cl.
*C07C 57/03* (2006.01)
*A61K 31/20* (2006.01)
*A23L 1/29* (2006.01)
*A23L 1/30* (2006.01)

(52) U.S. Cl.
CPC ............... *C07C 57/03* (2013.01); *A61K 31/20* (2013.01); *A23L 1/296* (2013.01); *A23L 1/3006* (2013.01)
USPC ........................................................ 514/560

(58) Field of Classification Search
None
See application file for complete search history.

(56) References Cited

U.S. PATENT DOCUMENTS

| 4,472,432 A | 9/1984 | Iwamura et al. |
| 2004/0186072 A1 | 9/2004 | Burstein et al. |
| 2010/0021956 A1 | 1/2010 | Shearer et al. |

FOREIGN PATENT DOCUMENTS

| EP | 1731602 | 12/2006 | |
| EP | 2161580 | 3/2010 | |
| WO | WO2010/028336 | * 3/2010 | ............. G01N 33/74 |

OTHER PUBLICATIONS

Fritsche et al. In Lipid/Fett 99(9), 314-318 (1997).*
Lopez-Garcia et al. In the Journal of Nutrition 135: 562-566 (2005).*
Mustad et al. In Metabolism Clinical and Experimental 55, 1365-1374 (2006).*
Stein et al. In the Journal of Clinical Investigation 100(2), 398-403 (1997).*
Goodman and Gilman's The Pharmacological Basis of Therapeutics (Tenth Edition (2001), McGraw Hill, Chapter I, pp. 3-29.*
Mayo Clinic Diabetes (in www.mayoclinic.org/diseases-conditions/type-2-diabetes/in-depth/diabetes-prevention/art-20047639?pg=2) (retrieved from the internet on Jan. 16, 2014).*
Alzheimer's Disease (in www.mayoclinic.org/diseases-conditions/alzheimers-disease/basics/prevention/CON-20023871) (retrieved from the internet on Jan. 16, 2014).*
Untreatable Neurodegenerative Diseases (in "machineslikeus.com/news/cure-untreatable-neurodegenerative-diseases") retrieved from the internet Jan. 14, 2014).*
Pereira et al. In JAMA 287:2081-2089 (2002).*
Månsson In Food & Nutrition Research vol. 55 (2008).*
Dhayal et al., British Journal of Pharmacology, 153:1718-1727 (2008). "Structural requirements for teh cytoprotective actions of mono-unstaruated fatty acids in the pancreatic β-cell line, BRIN-BD11."
Dorfman et al., Obesity, 17:1200-1207 (2009). "Metabolic Implications of Deitary Trans-fatty Acids."
Huang et al., Nutrition Research, 29:206-212 (2009). "Trans fat intake lowers total cholesterol and high-density lipoprotein cholesterol levels without changing insulin sensitivity index in Wistar rats."
Koppe et al., Am J Physiol Gastrointest Liver Physiol, 297:G378-G384 (2009). Trans fat feeding results in higher serum alanine aminotransferase and increased insulin resistance compared with a standard murine high-fat diet.
Lovejoy et al., Metabolism, 50(1):86-092 (2001). "Relationship of Dietary Fat and Serum Cholesterol Ester and Phospholipid Fatty Acids to Markers of Insulin Resistance in Men and Women With a Range of Glucose Tolerance."
Machado et al., J. Nutr., 140:1127-1132 (2010). "Intake of trans Fatty Acids Causes Nonalcoholic Steatohepatitis and Reduces Adipose Tissue Fat Content."
Mensink, Current Opinion in Lipidology, 16:27-30 (2005). "Metabolic and health effects of isomeric fatty acids."
Nestel, Journal of the American College of Nutrition, 27(6):735S-740S (2008). "Effects of Dairy Fats within Different Foods on Plasma Lipids."
Papantoniou et al., Eur J Nutr, 49:357-364 (2010). "Trans Fatty acid consumption, lifestyle and type 2 diabetes prevalence in a Spanish population."
Siguel et al., The American Journal of Cardiology, 71:916-920 (1993). "Trans-Fatty Acid Patterns in Patients with Angiographically Documented Coronary Artery Disease."
Stein et al., J. Clin. Invest.,100(2):398-403 (1997). "The Insulintropic Potency of Fatty Acids Is Influenced Profoundly by Their Chain Length and Degree of Saturation."
Sundram et al., Nutrition and Metabolism, 4:3 (2007). "Searic acid-rich interesterified fat and trans-rich fat raise the LDL-HDL ratio and plasma glucose relative to palm olein in humans."
Tardy et al., J. Lipid Res, 49:1445-1455 (2008). "Effects of trans MUFA from dairy and industrial sources on muscle mitochondrial function and insulin sensitivity."

* cited by examiner

*Primary Examiner* — Dennis Heyer
(74) *Attorney, Agent, or Firm* — Nixon Peabody LLP; David S. Resnick

(57) ABSTRACT

The present invention provides for a novel lipokine, trans-C16:1n7-palmitoleate, which also serves as a biomarker for metabolic status. More specifically, low concentrations of trans-C16:1n7-palmitoleate the serum indicates a risk of metabolic disease. Additionally, administering trans C16:1n7-palmitoleate to a subject (via pharmaceutical, nutraceutical, or other means), positively impacts glucose metabolism.

1 Claim, 3 Drawing Sheets

USE OF TRANS-PALMITOLEATE IN IDENTIFYING AND TREATING METABOLIC DISEASE

GOVERNMENT SUPPORT

This invention was made with government support under grants R01-HL085710, DK064360, DK71507-04, awarded by the National Institutes of Health. The U.S. government has certain rights in the invention.

CROSS-REFERENCE TO RELATED APPLICATIONS

This application is a 35 U.S.C. §371 National Phase Entry Application of International Application No. PCT/US2011/043517 filed Jul. 11, 2011, which designates the U.S., and which claims benefit under 35 U.S.C. §119(e) of U.S. Provisional Patent Application No. 61/362,838, filed Jul. 9, 2010, and U.S. Provisional Patent Application No. 61/373,956, filed Aug. 16, 2010, the contents of which are incorporated fully herein by reference in their entireties.

FIELD OF THE INVENTION

The present invention relates to molecular biology and cell metabolism. More specifically, embodiments of the present invention provide for a novel lipokine, trans-C16:1n7-palmitoleic acid (trans-palmitoleate), and its association with a better metabolic profile and lower incidence of diabetes. Other embodiments provide for trans-palmitoleate pharmaceutical, dietary and nutraceutical formulations, and dietary supplements, for the prevention and/or treatment of metabolic disease.

BACKGROUND

In recent years, the world has seen an alarming increase in metabolic diseases including obesity, insulin resistance, diabetes, fatty liver disease, and atherosclerosis. For example, over twenty million children and adults in the U.S., or 8% of the population, suffer from diabetes. Atherosclerosis is a leading cause of coronary heart disease and stroke, killing more than 600,000 Americans annually: more than 25% of all deaths in the U.S.

Dysregulation of tissue lipid composition or metabolism can lead to disruption of systemic insulin action and glucose metabolism in adipose, muscle, and liver tissues. Recent studies have clearly identified adipose tissue as a critical site for whole body metabolic regulation. A growing body of evidence supports the concept that peptides and hormones produced within the adipose tissue constitute an important component of the endocrine effects of this site on systemic carbohydrate and lipid homeostasis. There have been important advances in the identification of these molecules and characterization of their biological functions. As the major storage site for body lipids, adipose tissue has also been studied intensively in regards to its role in metabolic regulation through lipids. Although equally critical as peptide hormones, this area has been more challenging to reduce into molecular entities and pathways.

There are two prevailing views about the role of adipose tissue lipid metabolism in metabolic syndrome. First, storage of lipids in adipose tissue has been suggested to protect other organs, especially those that are not well equipped for such burden, from exposure to excessive lipids and thereby reducing the risk of lipotoxicity. Second, fatty acids derived from adipose tissue, particular under pathological conditions like obesity, could disrupt the function of peripheral tissues, resulting in muscle insulin resistance or increased triglyceride accumulation in liver. In these models, the principle consideration has often been the total amount of fatty acid exposure at different target tissues.

Serum fatty acids represent a very complex entity, however, and are composed of structures with varying chain lengths and degrees of saturation. The concentration and composition of fatty acids vary significantly under different physiological and pathological conditions, and these changes are not uniform between cell types and tissues. Although it is unlikely that the total fatty acid levels, alone, could be sufficiently informative, there has been some progress in addressing how different compositions of fatty acids in tissues or circulation may affect the metabolic output locally or systemically, but this has been experimentally challenging. Another intractable question has been how to address lipid storing and/or disposing in tissues responding to the dietary fatty acid intake, and how to adjust the composition to modulate metabolic outcomes. Hence, there remains a need for better understanding of the regulation of systemic fatty acid metabolism, and development of further diagnosis and treatment of fatty acid metabolism-related illnesses.

SUMMARY

The embodiments of the present invention derive from the surprising discovery that circulating trans-C16:1n7-palmitoleate is associated with less insulin resistance, less atherogenic dyslipidemia, and substantially lower diabetes incidence in humans. The present invention provides for a novel role for trans-palmitoleate as an important protector against metabolic risk pathways.

Hence, an embodiment of the present invention provides for a lipid diagnostic marker, trans-C16:1n7-palmitoleate, for monitoring metabolic homeostasis and diseases, such as diabetes and fatty liver diseases. In one embodiment, the monitoring comprises measuring the concentration of trans-C16:1n7-palmitoleate in the serum of a subject, wherein a low concentration is associated with increased risk for metabolic disease. In a related embodiment, increased trans-C16:1n7-palmitoleate is a biomarker of protection against metabolic syndrome or metabolic disease, including inflammatory disease, atherosclerosis, asthma, neurodegenerative disease, and other sequelae of dyslipidemia. For example, a serum concentration of less than about 0.16% trans-palmitoleate as % total fatty acids indicates a higher risk for diabetes than is a serum concentration of 0.20% trans-palmitoleate. As another example, a serum concentration of less than about 0.13% trans-palmitoleate as % total fatty acids indicates a higher risk for inflammatory disease than is a serum concentration of 0.20% trans-palmitoleate. The monitoring can be achieved, at least in part, using a computer system comprising a processor and a non-transitory program storage device readable by the computer system.

Additional embodiments of the present invention provide for the uses of trans-C16:1n7-palmitoleate as a biomarker for metabolic healthiness and the risk for metabolic diseases, and as an insulin-sensitizing hormone that improves glycemic control/glucose metabolism.

Other embodiments provide for a pharmaceutical formulation, a nutraceutical formulation or a diet supplement, comprising C16:1n7-palmitoleate in a substantially trans-form. The formulations and/or compositions can include 1% to 10% trans-palmitoleate, inclusive. For example, formulations and/or compositions can include at least 5% trans-palmitoleate or at least 6% trans-palmitoleate. Alternatively, for example, a daily or twice-daily supplement formulation and/or composition can include 10 mg to 500 mg trans-palmitoleate, inclusive, such as 50 mg or 100 mg trans-palmitoleate. Yet another embodiment provides for a composition with therapeutic utility for preventing and/or treating metabolic disorders, such as diabetes and fatty liver diseases, comprising C16:1n7-palmitoleate in a substantially trans-form.

In one embodiment, the invention provides a pharmaceutical formulation comprising C16:1n7-palmitoleate in a substantially trans-form. Another aspect of the present invention relates to a pharmaceutical formulation that provides palmitoleate delivery to an individual, wherein the palmitoleate is substantially trans-palmitoleate. The pharmaceutical formulation may be for enteral or parenteral administration.

In one embodiment, the invention provides a dietary formulation comprising C16:1n7-palmitoleate in a substantially trans-form. Another aspect of the present invention relates to a dietary formulation, or a dietary supplement, that provides palmitoleate delivery to an individual, wherein the palmitoleate is substantially trans-palmitoleate.

In one embodiment, the dietary formulation or supplement further comprises additional components such as one or more essential fatty acids, a source of carbohydrate, a source of protein, a source of vitamins and minerals, and an emulsifier.

In one embodiment, the dietary formulation further comprises a source of carbohydrate. The source of carbohydrates can be any simple or complex carbohydrate, e.g., monosaccharides, disaccharides, or oligosaccharides. In one embodiment the source of carbohydrate is at least one of corn starch, dextrose, and glucose.

In one embodiment, the dietary formulation further comprises a source of protein. The source of protein can be any protein hydrolysate or peptide mixtures, amino acid mixtures of high biologic values, e.g., meat, milk, egg or soy proteins. The protein hydrolysate can be partially hydrolyzed in nature and include a substantial fraction of variable chain length peptides, e.g., medium or short chain peptides, e.g., di- and tri-peptides, but have less than about 10% free amino acids, more preferably less than about 5% free amino acids. In one embodiment, only the highest biological value proteins are hydrolyzed, e.g., whey, lactalbumin, casein, egg white, egg solids, soy, or delactosed milk solids. In other embodiments, the protein source is lactose-free, and free amino acids are avoided in the formulation.

In one embodiment, the dietary formulation further comprises a source of vitamins and minerals. For example, vitamins and minerals in accordance with, or approximately, the Recommended Dietary Allowance (RDA), now called the Daily Reference Intake (DRI). The dietary formulations can also contain nutrients not recommended by the DRI, e.g., nucleotides, beta-carotene, carnitine, and taurine.

In one embodiment, the dietary formulation further comprises an emulsifier or other inactive ingredients such as sweeteners and/or flavorings, which can be artificial.

The dietary formulations of the present invention may be in the form of a dietary supplement (food oil) or used in a feeding regimen. In one embodiment, the dietary formulation is provided in a form suitable for oral administration. The dietary formulation can contain all essential amino acids, as well as essential vitamins and minerals to ensure that the recipient is obtaining all necessary nutrients. When the formulation is in the form of a dietary supplement (food oil), the formulation should provide about 5% to 60% of total energy expenditure in terms of calories.

In still another aspect of the invention, a method of treating/preventing a metabolic disease or disorder in a subject is provided, comprising administering to the subject a formulation that comprises palmitoleate, wherein the palmitoleate is substantially trans-palmitoleate. The metabolic disease can be diabetes, insulin resistance, fatty liver disease, and/or atherogenic dyslipidemia. The formulation may be administered parenterally or enterally. A form suitable for oral administration may be a dietary formulation. The dietary formulation can further comprise a source of carbohydrates, a source of proteins, a source of vitamins and minerals, and/or an emulsifier or other inactive ingredients, such as sweeteners and/or flavorings.

In still another aspect of the invention, a method of improving the glucose metabolism in a subject with insulin resistance is provided. The method comprises administering to said subject a pharmaceutical formulation or a dietary formulation that comprises palmitoleate, wherein the palmitoleate is substantially trans-palmitoleate. The dietary formulation can further comprise a source of carbohydrates, a source of proteins, a source of vitamins and minerals, and/or an emulsifier or other inactive ingredients, such as sweeteners and/or flavorings.

In another aspect of the invention, a method of reducing the level of an inflammatory biomarker in a subject, that indicates an inflammatory condition, is provided. The method comprises administering to the subject a pharmaceutical formulation comprising a substantially trans-form of palmitoleate, wherein the formulation is administered in an amount sufficient to reduce the level the inflammatory biomarker. The administration may be parenteral or oral.

In yet another aspect of the invention, a method of reducing the level of an inflammatory biomarker in a subject, that indicates an inflammatory condition, is provided. The method comprises administering to the subject a pharmaceutical or nutraceutical (e.g., dietary) formulation comprising a substantially trans-form of palmitoleate, wherein the formulation is administered in an amount sufficient to reduce the level the inflammatory biomarker. The formulation comprises palmitoleate, wherein the palmitoleate is substantially trans-palmitoleate, and can be a dietary formulation in the form of an oil emulsion, or in the form of food oil suitable for oral administration. The dietary formulation can further comprise a source of carbohydrates, a source of proteins, a source of vitamins and minerals, and/or an emulsifier or other inactive ingredients, such as sweeteners and/or flavorings.

DETAILED DESCRIPTION

Figure 1:
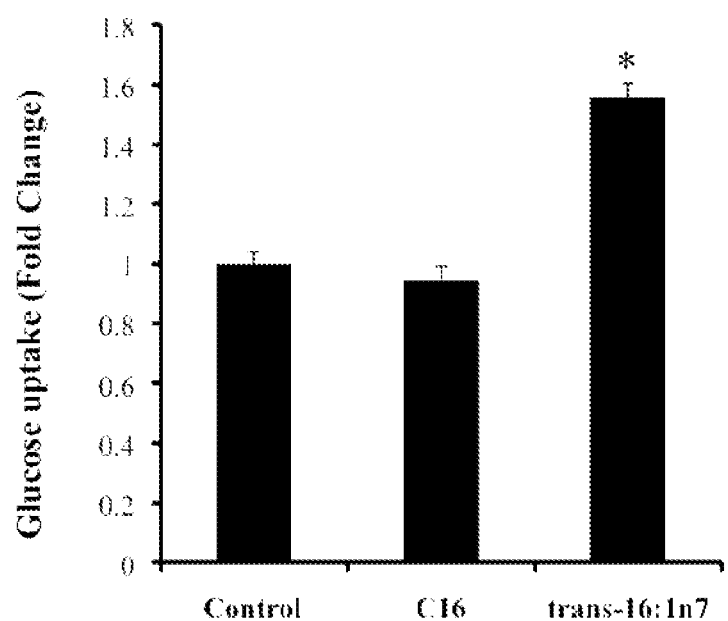
FIG. 1 is a bar graph showing data from differentiated C2C12 myotubes that were incubated with control medium, or medium with 0.25 mM palmitate (C16) or trans-16:1n7-palmitoleate for 6 hours; glucose uptake was assayed as described herein. *, significantly different from control.

The present invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

The present invention is based on the surprising discovery that circulating trans-C16:1n7-palmitoleate is associated with less insulin resistance, less atherogenic dyslipidemia and substantially lower diabetes incidence in humans. Animal experiments have demonstrated metabolic benefits of circulating cis-palmitoleate (cis-16:1n-7) derived from adipocyte fatty-acid-synthesis (FS). In humans, cis-palmitoleate is largely hepatic-derived, with complex determinants. In contrast, trans-palmitoleate (trans-C16:1n7) is a distinctly exogenous, dietary isomer of cis-16:1n-7, and the exploration of its role in human metabolism is in unconfounded by endogenous FS or its determinants. As described herein, higher levels of trans-palmitoleate are associated with a better metabolic profile and lower incidence of diabetes.

The present inventors investigated relationships of circulating trans-palmitoleate levels with metabolic risk and incident diabetes mellitus among 3,736 U.S. men and women in the prospective Cardiovascular Health Study. Plasma phospholipid fatty acids, anthropometry, blood lipids, inflammatory markers, and glucose-insulin levels were measured at baseline using standardized methods. Independent determinants of trans-palmitoleate and relationships of trans-palmitoleate with metabolic risk factors were investigated using multivariable-adjusted linear regression. Relationships with incident diabetes (304 incident cases) were investigated using Cox proportional-hazards. Validation for metabolic risk factors was performed in a second independent cohort of 327 generally healthy women.

In this multivariable-analyses, older age, male sex, non-white race, education, and whole-fat dairy consumption were major predictors of higher trans-palmitoleate. Higher trans-palmitoleate was associated with slightly lower adiposity and, independent of this, higher HDL-C (across quintiles: +1.9%, P=0.04), lower triglycerides (−19.0%, P<0.001), lower total:HDL-C (−4.7%, P<0.001), lower CRP (−13.8%, P=0.05), and lower HOMA-IR (−16.7%, P<0.001). Trans-palmitoleate was also associated with substantially lower incident diabetes, with multivariable-RR's of 0.79 (95% CI=0.54-1.15), 0.89 (95% CI=0.58-1.33), 0.41 (95% CI=0.27-0.64), and 0.38 (95% CI=0.24-0.62) in quintiles 2-5 vs. 1 (P-trend<0.001). Findings were independent of dairy consumption in general and other fatty acid biomarkers including pentadecanoic acid (15:0), palmitic acid (17:0), and vaccenic acid (18:1 trans-11). Protective associations with metabolic risk factors were confirmed in the validation cohort. In sum, circulating trans-palmitoleate is associated with less insulin resistance, less atherogenic dyslipidemia, and substantially lower diabetes incidence.

Fatty acids are powerful modulators of metabolic and physiologic function, but effects of many individual fatty acids are not well understood. Palmitoleic acid (cis-16:1n7) is produced during fatty acid synthesis (FS), also termed de novo lipogenesis, the process of converting glucose into fatty acids. It was demonstrated recently that genomic deletion of adipose tissue fatty-acid-binding-protein (FABP)-4 in mice resulted in the activation of adipose tissue FS, which significantly increased blood palmitoleate and directly protected against hepatic and skeletal muscle insulin resistance and related metabolic abnormalities. Cao et al., 134 Cell 933 (2008); WO 10/028336. These benefits appeared partly related to suppression of hepatic-FS, suggesting that circulating palmitoleate may function as a "lipokine" to provide counter-regulatory feedback against hepatic-FS. Some in vitro experimental models provide support for metabolic benefits of palmitoleate, including in adipocytes, macrophages, skeletal muscle cells, and pancreatic beta cells. Dimopoulos et al., 399 Biochem. J. 473 (2006); Sauma et al., 22 Nutr. 60 (2006); Maedler et al., 52 Diabetes 726 (2003); Eerbay et al., 15 Nat. Med. 1383 (2009).

The investigation of metabolic effects of circulating palmitoleate in humans continues. Lifestyle determinants of endogenous palmitoleate production are complex and include high carbohydrate diets (Hudgins et al., 97 J. Clin. Invest. 2081 (1996); Marques-Lopes et al., 73 Am. J. Clin. Nutr. 253 (2001); Schwarz et al., 77 Am. J. Clin. Nutr. 43 (2003); King et al., 83 Am J. Clin. Nutr. 227 (2006); Hudgins et al., 19 J. Nutr. Biochem. 237 (2008); Chong et al., Am. J. Clin. Nutr. 87 Am. J. Clin. Nutr. 817 (2008)); alcohol use (Mozaffarian et al., 92 Am. J. Clin. Nutr. 1350 (2010); Warnet et al., 290 Br. Med. J. 1859 (1985)); and excess energy balance with conversion of excess carbohydrate energy into fat for long-term storage (Cao et al., 2008; Mozaffarian et al., 2010; Fukuchi et al., 229 Exp. Biol. Med. 486 (2004)).

Thus, metabolic effects of endogenously-produced cis-palmitoleate in humans might be somewhat confounded by these different factors and related weight gain and adiposity. In the present cohort, for example, it was found previously that higher plasma phospholipid palmitoleate was associated with more favorable levels of LDL-C, HDL-C, total:HDL-C, and fibrinogen, but also greater adiposity, triglycerides, and (in men) insulin resistance; and with no overall associations with incident diabetes, perhaps related to these competing benefits vs. confounders. Mozaffarian et al., 2010. Additionally, the source of endogenous palmitoleate production may alter its metabolic effects. In animal-models, metabolic benefits were derived from suppression of hepatic-FS by a non-hepatic source of palmitoleate. Cao et al., 2008. With typical modern diets, adipose-FS and palmitoleate production are largely quiescent, however, and hepatic-FS dominates. Cao et al., 2008; Hudgins et al., 1996; Marques Lopes et al., 2001; Schwarz et al., 2003; King et al., 2006; Hudgins et al., 2008; and Chong et al., 2008.

Due to complexities of both divergent lifestyle determinants and tissue sources of endogenously-produced palmitoleate, investigation of an exogenous, non-hepatic source of palmitoleate would be ideal to help elucidate its role in human metabolic risk. Dietary sources of palmitoleate are very unusual (Maguire et al., 55 Intl. J. Food Sci. Nutr. 171 (2004), and furthermore the cis-palmitoleate isomer found in most such sources can not be differentiated from endogenously-produced cis-palmitoleate as a circulating biomarker. In contrast, a trans isomer of palmitoleate (trans-16:1n-7) is also consumed in the diet. Because mammals synthesize carbon-carbon double bonds in the cis configuration, trans-palmitoleate represents a distinctly exogenous source of 16:1n-7, unconfounded by endogenous FS or its determinants. Whereas trans fats from partially hydrogenated vegetable oils produce unfavorable effects on cardiovascular risk (Mozaffarian et al., 354 N. Engl. J. med. 1601 (2006), trans-palmitoleate is principally derived from ruminant (e.g., dairy) fats (Micha et al., 91 Am. J. Clin. Nutr. 883 (2010), which have not been associated with higher risk (Mozaffarian et al., 2006). Indeed, some long-term cohorts have found inverse associations between dairy consumption and risk of insulin resistance or metabolic syndrome. Elwood et al., 27 J. Am. Coll. Nutr. 723S (2008); Tremblay & Gilbert, 28 J. Am. Coll. Nutr. 91S (2009). None of these prior studies, however, have evaluated the potential metabolic role of trans-palmitoleate.

The present inventors investigated the relationship between plasma phospholipid trans-palmitoleate and metabolic risk factors and incident diabetes mellitus among 3,736 U.S. men and women in the Cardiovascular Health Study (CHS), an NLHBI-sponsored prospective cohort study among older adults. Validation for metabolic risk factors was performed in a second independent cohort of 327 generally healthy women. Higher levels of trans-palmitoleate were associated with a better metabolic profile and lower incidence of diabetes.

More specifically, the mean±SD levels of trans-palmitoleate were low: 0.18±0.05%, range=0.02, 0.55%. Among other phospholipid fatty acids, trans-palmitoleate levels correlated most with 15:0 (r=0.64) and 17:0 (r=0.66), odd-chain-length fatty acid biomarkers of dairy fat consumption (Wolk et al., 68 Am. J. Clin. Nutr. 291 (1998); Wolk et al., 131 J. Nutr. 823 (2001); Brevik et al., 59 Eur. J. Clin. Nutr. 1417 (2005)), but weakly with other trans-fats, most largely derived from partially hydrogenated oils (Micha et al., 2010), including trans-16:1n-9 (r=0.11), trans-18:1n-7 (r=0.25), total trans-18:1 (r=0.15), and total trans-18:2 (r=0.07). In bivariate (unadjusted) analyses (Table 1), trans-palmitoleate was associated with slightly older age, white race, and modestly less prevalent coronary heart disease (CHD) and diabetes:

Trans-palmitoleate was also associated with less alcohol use, modestly higher total fat intake, modestly lower carbohydrate and low-fat dairy consumption, and greater consumption of whole-fat dairy foods and red meat.

To elucidate and quantify the independent determinants of circulating trans-palmitoleate, we investigated potential demographic, clinical, and lifestyle predictors in this large cohort of free-living adults (Table 2):

TABLE 2

Multivariable-Adjusted Predictors of Plasma Phospholipid Trans-Palmitoleate

| | | SD Difference (95% CI) in Trans-Palmitoleic Acid* | P value |
|---|---|---|---|
| Age, each 5 years | | 0.08 (0.04, 0.12) | <0.001 |
| Sex | Male | reference | |
| | Female | −0.25 (−0.34, −0.16) | <0.001 |
| Race | White | reference | |
| | Nonwhite | 0.33 (0.19, 0.48) | <0.001 |
| Education | Less than high school | reference | |
| | High school graduate | 0.07 (−0.04, 0.18) | 0.22 |
| | Some college | 0.14 (0.02, 0.27) | 0.02 |
| | College graduate | 0.16 (0.03, 0.29) | 0.03\2 |
| Prevalent diabetes | No | reference | |
| | Yes | −0.03 (−0.14, 0.09) | 0.63 |
| Prevalent CHD | No | reference | |
| | Yes | −0.14 (−0.23, −0.04) | 0.007 |
| Smoking | Never | reference | |
| | Former | −0.04 (−0.13, 0.05) | 0.41 |
| | Current | 0.09 (−0.06, 0.24) | 0.26 |
| Body mass index, each kg/m2 | | −0.01 (−0.02, −0.00) | 0.004 |
| Leisure-time activity, each 500 kcal/wk | | −0.01 (−0.02, 0.01) | 0.28 |
| Alcohol, each drink/week | | −0.03 (−0.04, −0.02) | <0.001 |
| Carbohydrate, each higher 5% E replacing fat† | | −0.05 (−0.08, −0.01) | 0.01 |
| Protein, each higher 5% E replacing fat† | | −0.08 (−0.16, 0.00) | 0.05 |

TABLE 1

Baseline plasma phospholipid trans-palmitoleate in 3,736 U.S. adults.

| | Sex-Specific Quintiles of Trans-Palmitoleic Acid | | | | | |
|---|---|---|---|---|---|---|
| | I | II | III | IV | V | |
| n | (n = 767) | (n = 738) | (n = 744) | (n = 748) | (n = 739) | |
| % of total fatty acids | 0.12 ± 0.02 | 0.16 ± 0.01 | 0.18 ± 0.01 | 0.21 ± 0.01 | 0.26 ± 0.03 | |
| Age, years | 75 ± 5 | 75 ± 5 | 75 ± 5 | 76 ± 5 | 76 ± 5 | * |
| Sex, % male | 43 | 47 | 45 | 46 | 46 | |
| Race, % white | 81 | 84 | 86 | 90 | 91 | * |
| Education > high school, % | 42 | 43 | 46 | 47 | 46 | * |
| Current smoking, % | 9 | 6 | 8 | 7 | 10 | |
| Coronary heart disease, % | 26 | 27 | 26 | 23 | 19 | * |
| Diabetes mellitus, % | 17 | 18 | 19 | 17 | 13 | * |
| Exercise intensity moderate+, % | 44 | 42 | 45 | 46 | 44 | |
| Leisure-time activity, kcal/wk | 1084 ± 1422 | 1056 ± 1433 | 1170 ± 1475 | 1063 ± 1471 | 943 ± 1269 | |
| Alcohol, drinks/week | 3.7 ± 10.3 | 2.2 ± 4.9 | 1.8 ± 4.6 | 1.6 ± 4.1 | 1.3 ± 3.9 | * |
| Total fat, % energy | 30.7 ± 6 | 31.6 ± 6 | 32.0 ± 6 | 32.8 ± 5 | 32.9 ± 6 | * |
| Carbohydrate, % energy | 53.8 ± 8 | 52.8 ± 8 | 52.4 ± 7 | 51.6 ± 7 | 51.5 ± 7 | * |
| Whole-fat dairy, servings/wk† | 5.7 ± 4.3 | 6.5 ± 4.8 | 6.7 ± 4.5 | 7.9 ± 4.9 | 8.7 ± 5.4 | * |
| Low-fat dairy, servings/wk† | 4.1 ± 3.7 | 4.3 ± 3.9 | 3.8 ± 3.4 | 3.8 ± 3.4 | 3.6 ± 3.7 | * |
| Red meat, servings/wk | 2.4 ± 2.2 | 2.5 ± 2.1 | 2.8 ± 2.2 | 3.1 ± 2.5 | 3.2 ± 2.5 | * |

Values are mean ± SD (continuous variables) or percent (categorical variables).
* P-trend<0.01 across quintiles.
†Whole-fat dairy foods include whole milk, 2% milk, cheese, butter, and ice cream. Low-fat dairy foods include 1% milk, skim milk, cottage cheese, and yogurt.

TABLE 2-continued

Multivariable-Adjusted Predictors of Plasma Phospholipid Trans-Palmitoleate

|  |  | SD Difference (95% CI) in Trans-Palmitoleic Acid* | P value |
|---|---|---|---|
| Whole-fat dairy | 0-2 servings/wk† | reference |  |
|  | 3-5 | 0.15 (0.01, 0.28) | 0.04 |
|  | 6-8 | 0.21 (0.08, 0.34) | 0.001 |
|  | 9-11 | 0.41 (0.27, 0.55) | <0.001 |
|  | 12-14 | 0.40 (0.24, 0.56) | <0.001 |
|  | 15+ | 0.69 (0.49, 0.89) | <0.001 |
| Low-fat dairy, each serving/d |  | −0.01 (−0.03, −0.00) | 0.03 |
| Red meat, each serving/d† |  | 0.14 (−0.00, 0.27) | 0.06 |

*Values are multivariable-adjusted associations of each potential predictor with trans-palmitoleic acid levels, evaluated per 1 SD, adjusted for each of the variables in the table simultaneously. A value of 1.00 would represent a 1 SD difference in trans-palmitoleate levels associated with the predictor
†Dietary habits were assessed 3 years earlier, in 1989-90, which would underestimate magnitudes of associations.
% E = percent energy.

In multivariable-adjusted analyses, older age, nonwhite race, and greater education were associated with higher trans-palmitoleate levels, and female sex and prevalent CHD were associated with lower levels. Greater body mass index and alcohol use were also associated with slightly lower levels. Among dietary predictors, whole-fat dairy consumption was the strongest predictor, with 0.69 SD higher trans-palmitoleate levels among those consuming 15+ servings/week (2+ servings/day), compared with ≤2 servings/week. This relationship appeared directly related to dairy fat content: evaluating different dairy foods simultaneously, relationships were strongest for whole milk (+0.49 higher SD of trans-palmitoleate per serving/day, p<0.001), then butter (+0.31, p<0.001), 2% milk (+0.21, p<0.001), cheese (+0.20, p=0.04), and ice cream (+0.18, p=0.09).

In multivariable-analyses adjusting for independent predictors of trans-palmitoleate plus other potential confounders, trans-palmitoleate levels were significantly associated with several metabolic risk factors (Table 3):

TABLE 3

Multivariable-adjusted relationships of plasma phospholipid trans-palmitoleate

|  | Quintiles of Trans-Palmitoleic Acid | | | | | |
|---|---|---|---|---|---|---|
|  | I | II | III | IV | V | P for Trend |
| % total fatty acids, median | 0.13 | 0.16 | 0.18 | 0.21 | 0.25 |  |
| Adiposity: | | | | | | |
| BMI, kg/m$^2$ | 26.7 | 27.0 | 26.8 | 26.9 | 26.2 | 0.06 |
| Waist circumference, cm | 97.7 | 98.4 | 97.2 | 97.4 | 96.0* | 0.009 |
| Blood Lipids: | | | | | | |
| LDL-C, mmol/L | 3.26 | 3.32 | 3.29 | 3.26 | 3.34 | 0.63 |
| LDL-C, mg/dl | 126 | 128 | 127 | 126 | 129 |  |
| HDL-C, mmol/L | 1.37 | 1.35 | 1.35 | 1.39 | 1.40 | 0.043 |
| HDL-C, mg/dl | 53.0 | 52.0 | 52.1 | 53.7 | 54.0 |  |
| Triglycerides, mmol/L | 1.66 | 1.51 | 1.45 | 1.36 | 1.34 | <0.001 |
| Triglycerides, mg/dl | 147 | 134† | 128‡ | 120‡ | 119‡ |  |
| Total/HDL-C ratio | 4.3 | 4.3 | 4.2 | 4.1† | 4.1† | <0.001 |
| Inflammation: | | | | | | |
| CRP, nmol/L | 27.6 | 26.7 | 24.8 | 25.7 | 23.8 | 0.05 |
| CRP, mg/L | 2.9 | 2.8 | 2.6 | 2.7 | 2.5 |  |
| Fibrinogen, μmol/L | 9.3 | 9.6‡ | 9.7‡ | 9.8† | 9.6‡ | 0.006 |
| Fibrinogen, mg/dl | 316 | 327† | 329‡ | 332‡ | 328† |  |
| Glucose-Insulin Homeostasis: | | | | | | |
| Fasting glucose, mmol/L | 5.7 | 5.8 | 5.7 | 5.7 | 5.7 | 0.10 |
| Fasting glucose, mg/dl | 104 | 105 | 103 | 103 | 103 |  |
| Fasting insulin, mU/l | 11.3 | 11.0 | 10.7 | 10.21† | 9.8‡ | <0.001 |
| HOMA-IR, units | 3.0 | 2.9 | 2.8* | 2.7† | 2.5‡ | <0.001 |
| Blood Pressure: | | | | | | |
| Systolic, mmHg | 137 | 136 | 136 | 136 | 136 | 0.48 |
| Diastolic, mmHg | 71 | 71 | 70 | 71 | 71 | 0.98 |

Values are adjusted means (transformed to approximate normality for analyses and re-transformed as necessary), adjusted for age (years), sex, race (white/nonwhite), education (<high school, high school, some college, college graduate), enrollment site (4 sites), smoking (never, former, current), diabetes (yes/no), coronary heart disease (yes/no), physical activity (kcal/wk), alcohol use (6 categories), and consumption of carbohydrate (% energy), protein (% energy), red meat (servings/week), whole-fat dairy foods (6 categories), low-fat dairy foods (5 categories), and total energy (kcal/d). Results for blood lipid, inflammatory, glucose-insulin, and blood pressure measures are also adjusted for body mass index (kg/m2) and waist circumference (cm).
*P < 0.05, †P < 0.01, ‡P < 0.001 compared with quintile 1.

Higher trans-palmitoleate was associated with slightly lower BMI (across quintiles: −1.8%, P=0.06) and waist circumference (−1.8%, P=0.009). In models further adjusted for these differences in adiposity, trans-palmitoleate was also associated with slightly higher HDL-C (+1.9%, P=0.04), substantially lower triglycerides (−19.0%, P<0.001), lower total: HDL-C ratio (−4.7%, P<0.001), and lower CRP (−13.8%, P=0.05). Trans-palmitoleate was also associated with higher fibrinogen (P=0.006), but this relationship appeared limited to lower levels in the lowest quintile only. When we evaluated measures of glucose-insulin homeostasis, trans-palmitoleate was associated with lower fasting insulin (−13.3%, P<0.001) and lower insulin resistance assessed by HOMA-IR (−16.7%, P<0.001). Trans-palmitoleate was not associated with LDL-C, fasting glucose, or BP (Table 3). All relationships appeared similar in analyses stratified by sex, with little evidence for interaction (P-interaction=NS for each).

Among 2,985 participants free of prevalent diabetes at baseline, 304 new cases of diabetes occurred during 27,866 person-years follow-up (incidence rate=10.9/1000 person-years). In age- and gender-adjusted analyses, trans-palmitoleate levels were associated with markedly lower risk of new-onset diabetes, including more than 2-fold lower risk in quintile 4 (RR=0.44, 95% CI=0.30-0.66) and nearly 3-fold lower risk in quintile 5 (RR=0.36, 95% CI=0.23-0.57), compared with quintile 1 (P-trend<0.001), as shown in Table 4:

justed RR of diabetes was 28% lower per each higher SD of trans-palmitoleate (RR=0.72, 95% CI=0.61-0.86, P<0.001).

Based on both biologic considerations and independent correlates in the present cohort (Table 2), consumption of carbohydrate, protein, red meat, and especially dairy foods could each confound the relationship between trans-palmitoleate and incident diabetes, even in fully multivariable-adjusted analyses. Whether these factors themselves independently associated with incident diabetes was evaluated. After full multivariable-adjustment (covariates as in Table 4) but excluding adjustment for trans-palmitoleate levels, neither consumption of carbohydrate (P=0.81), protein (P=0.88), red meat (p=0.69), nor low-fat dairy (p=0.98) were significantly associated with incident diabetes.

Conversely, greater whole-fat dairy consumption was associated with lower risk (across six categories, P-trend=0.03). When further adjusted for trans-palmitoleate levels, the association between whole-fat dairy consumption and diabetes risk was attenuated and no longer significant (P-trend=0.17), whereas the relationship between trans-palmitoleate and diabetes risk was robust even with adjustment for dairy consumption (Table 4).

These findings suggested that trans-palmitoleate was the principal determinant of the protective association. These results could partly relate to trans-palmitoleate being measured as an objective biomarker, however, whereas dairy con-

TABLE 4

Correlation between Diabetes Mellitus and plasma phospholipid trans-palmitoleate

| | Quintiles of Trans-Palmitoleic Acid | | | | | P for trend |
|---|---|---|---|---|---|---|
| | I | II | III | IV | V | |
| Person-years of follow-up | 5,595 | 5,435 | 5,556 | 5,811 | 5,469 | |
| No. of incident cases | 93 | 68 | 59 | 46 | 38 | |
| | Hazard ratio (95% confidence interval) | | | | | |
| Age- and sex-adjusted | 1.0 (reference) | 0.84 (0.57-1.22) | 0.88 (0.59-1.31) | 0.44 (0.30-0.66) | 0.36 (0.23-0.57) | <0.001 |
| Multivariate-adjusted | 1.0 (reference) | 0.79 (0.54-1.15) | 0.89 (0.58-1.33) | 0.41 (0.27-0.64) | 0.38 (0.24-0.62) | <0.001 |

For Table 4, incident diabetes was defined by new use of insulin or oral hypoglycemic medication, fasting glucose ≥126 mg/dl, or 2-hour postchallenge glucose ≥200 mg/dl, excluding individuals with prevalent diabetes at baseline. Multivariable model adjusted for age (years), gender (male/female), race (white/nonwhite), education (<high school, high school, some college, college graduate), enrollment site (four sites), smoking (never, former, current), body mass index (kg/m$^2$), waist circumference (cm), coronary heart disease (yes/no), physical activity (kcal/wk), alcohol use (six categories), and consumption of carbohydrate (% energy), protein (% energy), red meat (servings/week), whole-fat dairy foods (6 categories), low-fat dairy foods (five categories), and total energy (kcal/d).

Additional adjustment for race, education, smoking, BMI, waist circumference, physical activity, and other clinical and lifestyle risk factors including consumption of dairy foods and red meat did not appreciably alter results (Table 4), suggesting that the relationship between trans-palmitoleate and incident diabetes was not appreciably confounded by these factors. This lower risk appeared similar in men (extreme-quintile RR=0.29, 95% CI=0.11-0.74) and women (extreme-quintile RR=0.41, 95% CI=0.24-0.71) (P-interaction=0.87). When evaluated continuously per SD, the multivariable-adsumption was estimated from a validated yet self-reported questionnaire. Whether other phospholipid fatty acid biomarkers of dairy consumption independently related to diabetes risk and also whether adjustment for these objective biomarkers attenuated the protective association for trans-palmitoleate were evaluated. After multivariable-adjustment (covariates as in Table 4), neither 15:0 (per SD, RR=1.01, 95% CI=0.92-1.11) nor 17:0 (per SD, RR=0.98, 95% CI=0.80-1.20) were independently associated with diabetes risk. In contrast, even with additional adjustment for levels of both 15:0 and 17:0, the relationship between trans-palmitoleate and new-onset diabetes was unchanged (extreme-quintile RR=0.39, 95% CI=0.22-0.69, P-trend<0.001). Similar analyses were performed for vaccenic acid (trans-18:1n-7), a proposed ruminant fat biomarker. Vaccenic acid was not independently associated with incident diabetes (RR per SD=0.89, 95% CI=0.77-1.03) nor substantially altered the lower risk seen with higher trans-palmitoleate (extreme-quintile RR=0.43, 95% CI=0.25-0.75, P-trend<0.001).

In the separate NHS validation cohort, higher erythrocyte trans-palmitoleate was associated with lower interleukin-6 (IL-6) (multivariable-adjusted levels across quartiles: 2.3 pg/ml vs. 1.8 pg/ml, P-trend=0.02) and CRP (3.3 vs. 2.1 mg/L, P-trend=0.02) and trends toward lower total:HDL-C (4.21 vs. 3.87, P-trend=0.10) and hemoglobinA1c (5.92 vs. 5.66, P-trend=0.06). In similar analyses, higher plasma trans-palmitoleate was associated with higher HDL-C (56.5 vs. 61.7 mg/dl, P-trend=0.03), lower total:HDL-C (4.28 vs. 3.63, P-trend<0.001), and lower hemoglobinA1c (5.88 vs. 5.64 percent, P-trend=0.03).

In this large prospective cohort, phospholipid trans-palmitoleate levels were independently associated with lower metabolic risk. Among risk factors, trans-palmitoleate was associated with slightly lower adiposity and, independent of this, higher HDL-C and appreciably lower triglycerides, total:HDL-C and insulin resistance. Prospectively, trans-palmitoleate was associated with substantially lower new-onset diabetes, with nearly 3-fold lower risk across quintiles. These findings were independent of adjustment for a broad range of demographic, clinical, lifestyle, and dietary factors. The lower risk was also independent of other objective biomarkers of dairy consumption and ruminant fat consumption. Furthermore, neither intake of whole-fat or low-fat dairy foods, phospholipid levels of vaccenic acid, nor phospholipid levels of other objective biomarkers of dairy fat consumption were independently associated with diabetes risk, supporting specificity of trans-palmitoleate as the relevant determinant. Protective associations with diabetes-related metabolic risk factors were confirmed in a separate validation cohort.

The magnitude and robustness of these relationships are notable. Appreciable independent associations were seen for small differences in trans-palmitoleate levels. Additionally, associations were not found for LDL-C or BP, suggesting specificity for insulin resistance and atherogenic dyslipidemia pathways rather than other metabolic pathways or better health in general. Intriguingly, the metabolic protection observed for trans-palmitoleate, a largely unstudied fatty acid produced by ruminant stomach bacteria and consumed in dairy and meats, paralleled the metabolic protection of adipocyte-produced endogenous cis-palmitoleate in FABP-deficient mice. Cao et al., 2008. Trans-palmitoleate, as an exogenous, nonhepatic source of palmitoleate, could partly suppress hepatic-FS or have other beneficial physiologic effects (e.g., augmenting skeletal muscle glucose uptake) by mimicking or competing with pathways of effect of either cis-palmitoleate (having a similar molecular structure but different bond configuration) or 16:0 (having a different bond structure but similar stereochemical shape). For example, this might be a normal counter-regulatory role of adipose-produced palmitoleate, that has been largely lost with modern diets that predominantly drive hepatic-FS.

The effects of trans-palmitoleate on FS or metabolic risk factors shown herein have not been reported previously. There is experimental evidence that ruminant trans-fatty acids could regulate FS, however. In bovine models, dietary trans-10/cis-12 conjugated linoleic acid (CLA) inhibits mammary gland FS by decreasing expression of lipogenic genes, including fatty acid synthetase and stearoyl-CoA desaturase (SCD) (Baumgard et al., 85 J. Dairy Sci 2155 (2002)), with compensatory up-regulation of adipose-FS genes, including fatty acid synthase, SCD, and FABP-4 (Harvatine et al., 139 J. Nutr. 849 (2009)). Additionally, one small study (n=191) in non-diabetic CHD patients found that platelet trans-palmitoleate levels were associated with a nonsignificant trend toward less coronary atherosclerosis (p=0.12); in comparison, other trans fats were associated with greater coronary atherosclerosis. Hodgson et al., 120 Atherosclerosis 147 (1996). The present invention provides the first evaluation of the relationships of trans-palmitoleate with metabolic risk markers and incident diabetes in humans.

Compared with other food sources of trans-fats, trans-palmitoleate appears relatively unique to ruminant-derived foods. Micha et al., 121 Circulation 2271 (2010). Hence, this isomer could plausibly have different biologic effects than industrially-produced trans fats. Consistent with this, consumption of ruminant trans fat has not been associated with higher cardiovascular risk; indeed, three cohorts have observed nonsignificant trends toward a protective relationship. Oomen et al., 357 Lancet 746 (2001); Pietinen et al., 145 Am. J. Epidemiol. 876 (1997); Jakobsen et al., 91 Am. J. Clin. Nutr. 1764 (2010); Willet et al., 341 Lancet 581 (1993)). This has been hypothesized to be due to potential benefits of ruminant vaccenic acid (trans-18:1n-7) or its metabolites (e.g., conjugated linoleic acids (CLA)). In metabolic feeding trials, however, trans-18:1n-7 consumption produced dose-dependent adverse effects on blood lipids—not benefits. Motard-Belanger et al., 87 Am. J. Clin. Nutr. 593 (2008); Chardigny et al., 87 Am. J. Nutr. 558 (2008).

The results presented herein suggest that trans-palmitoleate may be a key mediator in ruminant fats' protective effects. Multiple large cohort studies (Pereira et al., 287 JAMA 2081 (2002); Azadbakht et al., 82 Am. J. Clin. Nutr. 523 (2005); Mirmiran et al., 29 Intl. J. Obes. 115 (2005); Choi et al., 165 Arch. intern. Med. 997 (2005); Rosell et al., 84 Am. J. Clin. Nutr. 1481 (2006); Elwwod et al., 61 J. Epidem. Commun. Health 695 (2007); Beydoun et al., 87 Am. J. Nutr. 1914 (2008); Vergnaud et al., 88 Am. J. Clin. Nutr. 1248 (2008)), although not all studies (Vergnaud et al., 2008; Snijder et al., 16 Obes. 706 (2006)), have reported recently that dairy consumption is inversely associated with risk of obesity, metabolic risk factors, or diabetes, with mixed findings as to potential differences between low-fat vs. whole-fat dairy. Pereira et al., 2002; Choi et al., 2005; Rosell et al., 2006; Beydoun et al., 2008; Liu et al., 29 Diabetes Care 1579 (2006).

Further, although dairy calcium and CLA are proposed potential mediators of these benefits, experimental studies of calcium have shown small effects compared with dairy intake (Zemel et al., 12 Obes. Res. 582 (2004); Harvey-Berino et al., 13 Obes. Res. 1720 (2005); Sun & Zemel, 134 J. Nutr. 3054 (2004)); and feeding trials of CLA have shown disappointingly increased insulin resistance, increased lipid peroxidation, and mixed effects on inflammation/immune function (Riserus et al., 79 Am. J. Clin. Nutr. 1146S (2004); Moloney et al., 80 Am. J. Clin. Nutr. 887 (2004); Smedman et al., 106 Clin. Sci. 67 (2004); Nugent et al., 59 Eur. J. Clin. Nutr. 742-50 (2005)). By contrast, the results presented herein indicate that trans-palmitoleate reduces insulin resistance and metabolic risk.

The present analyses have several strengths. Information on fatty acid levels, metabolic risk factors, other sociodemographic and clinical factors, and diabetes incidence were prospectively collected in a well-established multicenter cohort study with little loss to follow-up. Biomarker fatty acid measurements provided objective measures of exposure. A large number of participants increased statistical power. Participants were randomly selected and enrolled from Medicare eligibility lists in several U.S. communities, providing a population-based sample and increasing generalizability. A wide number of demographic, lifestyle, and dietary covariates were available for multivariable-adjustment, minimizing residual confounding.

Associations between trans-palmitoleate and metabolic risk factors were cross-sectional, perhaps limiting assessment of temporality. Results for diabetes incidence are prospective and concordant with cross-sectional findings. Although several major metabolic risk factors were adjusted simultaneously, residual confounding by unknown or unmeasured factors may occur. Conversely, magnitudes of many of the multivariable-adjusted findings, in particular nearly 3-fold lower diabetes incidence, makes it improbable that residual confounding could fully account for these relationships. Furthermore, the protective associations of trans-palmitoleate were independent of estimated dietary intake and objective fatty acid biomarkers of dairy consumption. Because fasting and post-challenge glucose were not measured every year, diabetes incidence might be underestimated, but such underestimation would be unrelated to baseline fatty acid measurements and would not introduce bias.

The results presented herein support a potentially substantial protective effect of trans-palmitoleate on metabolic risk and diabetes incidence in humans. These novel findings suggest that this fatty acid may play an important role in pathways related to insulin resistance and atherogenic dyslipidemia.

Trans-palmitoleate is available commercially, for example, from Nu-Check Prep Inc. (Elysian, Minn.), Matreya, LLC (Pleasant Gap, Pa.), and Pfaltz & Bauer (Waterbury, Conn.). Additionally, trans-palmitoleate is produced by bacteria in the ruminant gut, and can be obtained for example, extraction and fractionation techniques. See, e.g., Chao et al., 70 J. Am. Oil Chemists' Soc. 139 (1993). Besides traditional "western" dairy products derived from cattle (*Bos taurus*), trans-palmitoleate is also present in, and can be obtained from, the milk of *Bos indicus*, (Brahmin cattle), sheep (*Ovis aries*), bubaline (water buffalo, *Bubalus bubalis*), goat (*Capra aegagrus hircus*), camel (*Camelus dromedarius*), and deer (*Cervus elaphus*). See, e.g., Aurelia et al., 63 Bull. USAMV-CN (2007). Regarding palmitoleate from ruminant meat sources, it has been reported that the palmitoleate content in steers can be increased by a grass silage diet, as opposed to clover silage diet. Lee et al., 76 Am. sci. 491 (2003). Trans-palmitoleate is also produced by microbes capable of being grown in mass culture, such as the commercially produced multicellular microalgae, *Spirulina platensis*. See, e.g., Diraman et al., 61 Israeli J. Aquaculture 134 (2009); Morist et al., 37 Process Biochem. 535 (2001). Hence, non-ruminant or "vegan" sources of trans-palmitoleate are available.

Additionally, cis-palmitoleate is readily available commercially and can be converted (isomerized) into trans-palmitoleate by, for example, sulfur, iodine, selenium, iodine and nickel catalysis. See Grompone & Tancredi, 29 Ind. Eng. Chem. Res. 1627 (1990); Grompone & Moyna, 63 J. Am. Oil Chemists' Soc. 1558 (1986). Cis-palmitoleate can be extracted from botanical sources such as Macadamia nut (*Macadamia integrifolia*) and Sea Buckthorn (*Hippophae rhamnoides*) oils, containing 17% and 40% of cis-palmitoleic acid, respectively, or from Chilean hazel nuts (*Gevuina avellana*). See, e.g., Li et al., SEA BUCKTHORN (*HIPPOPHAE RHAMNOIDES* L.): PRODUCTION & UTILIZATION (NRC Res. Press, 2003). Further, palmitoleate can be formed directly from the saturated fatty acid, palmitate, by the action of Δ9 desaturase enzymes (e.g., stearoyl-CoA desaturase-1) and then converted into the trans-form.

Hence, embodiments of the invention provide for a pharmaceutical formulation comprising C16:1n7-palmitoleate in substantially trans-form. The formulation may also include prodrugs, metabolites, derivatives or analogs of trans-palmitoleate. Generally speaking, a prodrug is a pharmacological substance (drug) administered in an inactive or less active form, that upon administration is metabolized in vivo into an active metabolite. Analogs, as envisioned herein, include structural analogs (compounds with a slightly altered chemical structure) and functional analogs (compounds with similar properties). Derivatives refer to compounds that are derived from a compound that is not similar in chemical or physical process. For example, chemical analogs or derivatives of trans-palmitoleate can be synthesized to hinder oxidation, or to make them less able to be formed into triglycerides. More specifically, for example, the carbohydrate head group may be modified (e.g., brominated, fluorinated, deuterated, etc.), to inhibit its reaction with the alcohol group on glycerol. If tolerated, such an analog may have a longer in vivo half-life as a free fatty acid. Additionally, deuterated analogs are known to have longer in vivo half-lives. See, e.g., Foster, 14 Advances Drug Res. 2 (1985); Oxtoby & Nachtrieb, PRINCIPLES OF MODERN CHEMISTRY 19 (3rd ed., 1996).

Particular structural analogs of trans-palmitoleate include, for example, analogs of trans-C161n7-palmitoleate with carboxylic acid bioesters, wherein the terminal carboxylic acid is replaced with, for example but not limited to, one of the following moieties:

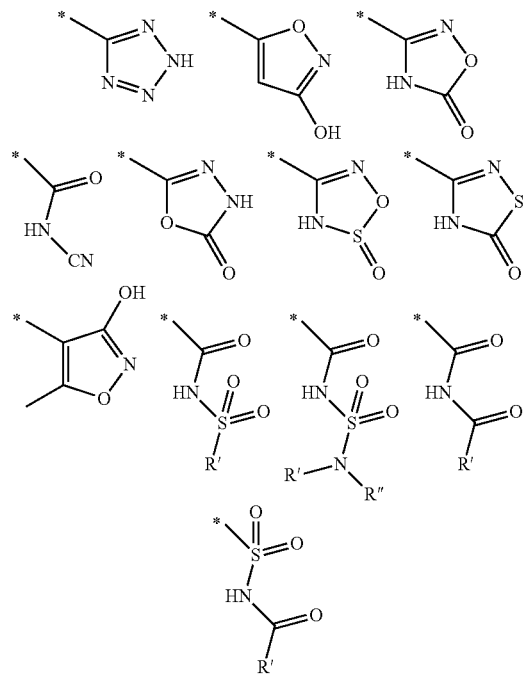

wherein R', R" is C1 to C6 alklyl or aryl, optionally, substituted.

The formulation may be for oral administration (e.g., enteral solids or liquids, buccal solids or liquids, respiratory tract solids, liquids or sprays) or parenteral injection or infusion (e.g., intradermal, subcutaneous, transdermal implant, intracavernous, intravetrial, transcleral, intracerebral, intrathecal, epidural, intravenous, intracardiac, intramuscular, intraosseous, or intraperitoneal injection).

In practice, the trans-palmitoleate formulations are administered in amounts sufficient to effect the desired change, such as an increase in insulin sensitivity in muscle tissue and/or decreased inflammation, and are used in the pharmaceutical form most suitable for such purposes.

For example, in pharmaceutical use, the trans-palmitoleate of the present invention is formulated for parenteral, particularly intravenous or subcutaneous, delivery according to conventional methods. The trans-palmitoleate formulation can be delivered intravenously, intraarterially or intraductally, or may be introduced locally at the intended site of action.

Intravenous administration can be by bolus injection or infusion over a typical period of one to several hours. In general, pharmaceutical formulations can include trans-palmitoleate in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. Methods of formulation are well known in the art and are disclosed, for example, in REMINGTON: SCIENCE & PRACTICE OF PHARMACY (19th ed., Gennaro, ed., Mack Pub. Co., Easton, Pa., 1995). Determination of dose is within the level of ordinary skill in the art. The trans-palmitoleate may be administered for acute treatment, over one week or less, often over a period of one to three days or may be used in chronic treatment, over several months or years. In general, a therapeutically effective amount of trans-palmitoleate is an amount sufficient to produce a clinically significant change in, for example, insulin sensitivity or inflammation. Trans-palmitoleate can also be beneficial in the treatment of metabolic syndrome or metabolic disease, including inflammatory disease, atherosclerosis, asthma, neurodegenerative disease, and other sequelae of dyslipidemia.

Injectable compositions are preferably aqueous isotonic solutions or suspensions, and suppositories are advantageously prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating or coating methods, respectively, and contain about 0.1% to 75%, such as about 1% to 50%, inclusive, of the active ingredient. More specifically, any of the pharmaceutical compositions discussed herein may contain 0.1% to 99%, such as 1% to 70% trans-palmitoleate, inclusive.

Liquid, particularly injectable compositions can, for example, be prepared by dissolving, dispersing, etc. The trans-palmitoleate is dissolved in or mixed with a pharmaceutically pure solvent such as, for example, water, saline, aqueous dextrose, glycerol, ethanol, polyethylene glycol and the like, to thereby form the injectable solution or suspension. Additionally, solid forms suitable for dissolving in liquid prior to injection can be formulated. Injectable compositions are preferably aqueous isotonic solutions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances.

The compounds and formulae of the invention can be administered in intravenous (both bolus and infusion), intraperitoneal, subcutaneous or intramuscular form, all using forms well known to those of ordinary skill in the pharmaceutical arts. Injectables can be prepared in conventional forms, either as liquid solutions or suspensions. Parenteral injectable administration is generally used for subcutaneous, intramuscular or intravenous injections and infusions. Additionally, one approach for parenteral administration employs the implantation of a slow-release or sustained-released systems, which assures that a constant level of dosage is maintained, according to U.S. Pat. No. 3,710,795.

The trans-palmitoleate compositions of the invention can also be administered in such oral dosage forms as immediate release, controlled release and/or sustained release tablets or capsules, pills, powders, granules, elixers, tinctures, suspensions, syrups and emulsions.

For oral administration in the form of a tablet or capsule (e.g., a gelatin capsule), a pharmaceutical-grade trans-palmitoleate can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, magnesium aluminum silicate, starch paste, gelatin, methylcellulose, sodium carboxymethylcellulose and/or polyvinylpyrrolidone, natural sugars such as glucose or β-lactose, corn sweeteners, natural and synthetic gums such as acacia, tragacanth or sodium alginate, polyethylene glycol, waxes and the like. Lubricants used in these dosage forms include sodium oleate, sodium stearate, magnesium stearate, sodium benzoate, sodium acetate, sodium chloride, silica, talcum, stearic acid, its magnesium or calcium salt and/or polyethyleneglycol and the like. Disintegrators include, without limitation, starch, methyl cellulose, agar, bentonite, xanthan gum starches, agar, alginic acid or its sodium salt, or effervescent mixtures, and the like. Diluents, include, e.g., lactose, dextrose, sucrose, mannitol, sorbitol, cellulose and/or glycine. An example capsule for oral consumption can contain 500 mg trans-palmitoleate.

The trans-palmitoleate of the invention can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is further hydrated with an aqueous solution of a drug to a form lipid layer encapsulating the drug, as described in U.S. Pat. No. 5,262,564.

For solid compositions, excipients include pharmaceutical grades of mannitol, lactose, starch, magnesium stearate, sodium saccharin, talcum, cellulose, glucose, sucrose, magnesium carbonate, and the like may be used. The trans-palmitoleate may be also formulated as suppositories using for example, polyalkylene glycols, for example, propylene glycol, as the carrier. In some embodiments, suppositories are advantageously prepared from fatty emulsions or suspensions.

It is also possible for the trans-palmitoleate of the invention to be coupled with soluble polymers as targetable drug carriers. Such polymers can include polyvinylpyrrolidone, pyran copolymer, polyhydroxypropyl-methacrylamide-phenol, polyhydroxyethylaspanamide-phenol, or polyethyleneoxide-polylysine substituted with palmitoyl residues. Furthermore, the trans-palmitoleate of the invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

The dosage regimen utilizing a trans-palmitoleate formulation is selected in accordance with a variety of factors including type, species, age, weight, sex and medical condition of the subject; the severity of the condition to be treated; the route of administration; the renal and hepatic function of the patient; and the particular trans-palmitoleate formulation employed. An ordinarily skilled physician or veterinarian can determine and prescribe the effective amount of the trans-palmitoleate required to prevent, counter or arrest the progress of the condition in light of the present specification.

Examples of formulations suitable for oral administration include, but are not limited to food oil present in, chewable tablets, quick dissolve tablets, effervescent tablets, reconstitutable powders, elixirs, liquids, solutions, suspensions, emulsions, tablets, multi-layer tablets, bi-layer tablets, capsules, soft gelatin capsules, hard gelatin capsules, caplets, lozenges, chewable lozenges, beads, powders, granules, particles, microparticles, dispersible granules, health bars, confections, animal feeds, cereals, yogurts, cereal coatings, foods, nutritive foods, functional foods and combinations thereof.

Oral dosages of the invention, when used for the indicated effects as an edible pharmaceutical, nutraceutical or dietary formulation, or dietary supplement, may contain trans-palmitoleate in an amount ranging from about 0.05 mg/day to 2000.0 mg/day, inclusive, such as 10 mg, 50 mg, 100 mg, 200 mg, 300 mg, 400 mg, 500 mg, 1000 mg, 2000 mg trans-palmitoleate. Compounds of the invention may be administered in a single daily dose, or the total daily dosage may be administered in divided doses of two, three or four times daily.

In one embodiment, the invention provides pharmaceutical, nutraceutical or dietary formulation, or dietary supplement, that provides trans-palmitoleic acid delivery to an individual, comprising C16:1n7-palmitoleate in a substantially trans-form. In particular embodiments, the amount of trans-palmitoleate can be about 1%, 2%, 3%, 4%, 5%, 6%, 7%, 8%, 9% or 10%, inclusive, of total fatty acids present in the formulation or supplement. Alternatively, the amount of trans-palmitoleate can be about 1% to 100%, inclusive, of the total weight of the formulation, not including excipients. In particular embodiments, the concentration of trans-palmitoleate is least 5% of total fatty acids present in the formulation. In particular embodiments, the concentration of trans-palmitoleate is least 6% of total fatty acids present in the formulation. In particular embodiments, the concentration of trans-palmitoleate is least 7% of total fatty acids present in the formulation. In the context of total diet, trans-palmitoleate can be included as, for example, 2% (wt %) of the total diet.

Another aspect of the present invention relates to a dietary formulation, or a dietary supplement, that provides palmitoleate delivery to an individual, wherein the palmitoleate is substantially trans-palmitoleate. Because pure trans-16:1n7 is insoluble at room temperature, it is easily delivered with solid food or in a solid formulation. The dietary formulation or supplement can comprise additional components, such as one or more essential fatty acids, a source of carbohydrates, a source of proteins, a source of vitamins and minerals, an emulsifier, sweeteners, colorants, or flavoring agents. For example, nutraceutical or dietary supplements can contain, for example, 500 mg trans-palmitoleate, and can, optionally, be formulated with other beneficial agents or vitamins. For example, a dietary supplement can include trans-palmitoleate (e.g., 50 mg to 2000 mg, inclusive; 100 mg, 500 mg, 1000 mg, or 2000 mg) and, optionally, one or more of the following: cis-palmitoleate (e.g., 100 mg to 2000 mg, inclusive), and omega-3 fatty acids: eicosapentaenoic acid (EPA) and docosahexaenoic acid (DHA) or metabolites of these, and, optionally, a source of chromium. Other alternative oral or injectable formulations can be tailored to the needs of diabetics, and can include, in addition to trans-palmitoleate, other 'anti-diabetic' agents such as metformin, insulin, DPP-IV inhibitors (e.g., Januvia® sitagliptin, Merck & Co, Inc.), GLP-1 agonists (e.g., Byetta® exenatide, Amylin Pharmaceutical/Lilly USA, LLC), sulfonylureas and meglitinides (drugs that stimulate insulin release from beta cells), α-glucosidase inhibitors, and/or TZD family (e.g., Avandia® rosiglitazone, GalxoSmithKline).

Additional optional components to a trans-palmitoleate-based supplement, nutraceutical include, for example, biotin (e.g., 300-2000 mcg), folic acid (e.g., 400 mcg) hyalurinic acid (e.g., 25 mg sodium hyaluronate), ubiquinon (Co Q-10, e.g., 5 mg), beta carotene (10K IU), tocopherols (e.g., 200 IU d-α tocopheryl), anti-oxidants, chlorophyll (e.g., 4 mg from spirulina), calcium (e.g., 250 mg), choline (e.g., 30 mg bitartrate), citrus bioflavanoid (e.g., 60 mg), hesperidin flavinoid (e.g., 2 mg), inositol (e.g., 50 mg), iodine (e.g., 150 mcg), lutien (e.g., 200 mcg), magnesium (e.g., 125 mg magnesium citrate), molybdemun triurate (e.g., 75 mcg), manganese amino acid chelate (e.g., 4 mg), niacinimide (e.g., 125 mg), para aminobenzoic acid (e.g., 25 mg), riboflavin (e.g., 25 mg), rutin citrus flavonoid glycoside (e.g., 25 mg), selenium (e.g., 70 mcg selenium monomethionine), ginseng root (e.g., 50 mg), sodium (e.g., 15 mg), thiamine (e.g., 25 mg), vitamin A (e.g., 5K IU retinol palmitate), vitamin B-12 (e.g., 200 mcg cyanacobalamin), vitamin B-6 (e.g., 50 mg pyridoxine HCl), vitamin C (e.g., 1 g ascorbic acid), vitamin D3 (e.g., 400 IU cholecalciferol), vitamin K (e.g., 80 mcg phytonadione), zinc (e.g., 15 mg), plant sterols, ginger root extract, nettle leaf extract, bamboo shoot extract, ylang-ylang oil (from the *Cananga odorata* tree), Omega-3 (e.g., 300 mg oleic acid), Omega-6 (e.g., 400 mg linoleic acid), Omega-9 (e.g., 100 mg linolenic acid), probiotics, and vegetable cellulose, glycerin, silica, beeswax, or other excipients.

The source of carbohydrates can be any simple or complex carbohydrate, e.g., monosaccharides, disaccharides, or oligosaccharides, such as corn starch, dextrose, and glucose. The source of protein can be any protein hydrolysate or peptide mixture, amino acid mixtures of high biologic values, e.g., meat, milk, egg or soy proteins. The protein hydrolysate can be partially hydrolyzed in nature and include a substantial fraction of variable chain length peptides, e.g., medium or short chain peptides, e.g., di- and tri-peptides, but have less than about 10% free amino acids, or less than about 5% free amino acids. For example, only the highest biological value proteins are hydrolyzed, e.g., whey, lactalbumin, casein, egg white, egg solids, soy, or delactosed milk solids. The protein source can be lactose-free, and/or avoid free amino acids. Vitamins and minerals can be added in accordance with the Daily Reference Intake (DRI). The dietary formulations can also contain nutrients not recommended by the DRI, e.g., nucleotides, β-carotene, carnitine, and taurine. The dietary formulation can further comprise an emulsifier or other inactive ingredients such as sweeteners and/or flavorings, which can be artificial. The dietary formulation or supplement in accordance with the present invention can further comprise additional components such as, antioxidants, chelating agents, osmolality modifiers, buffers, neutralization agents and the like that improve the stability, uniformity and/or other properties of the formulation.

The dietary formulations of the present invention may be in the form of a dietary supplement (food oil) or used in a feeding regimen, and as such can be provided in a form suitable for oral administration. The dietary formulation can contain all essential amino acids, as well as essential vitamins and minerals to ensure that the recipient is obtaining all necessary nutrients. When the formulation is in the form of a dietary supplement (food oil), the formulation can provide about 5% to 60% of total energy expenditure in terms of calories. Use of such a supplement is expected to produce the same beneficial results as described herein for the dietary formulations when combined with a diet. The dietary formulation or supplement can also be made in powder form by increasing the percent total solids of the formula, using procedures well known to those skilled in the art. The concentrate or powder can then reconstituted for feeding by adding water (tap or deionized-sterilized water).

The dietary formulation described herein can further comprise a therapeutic agent beyond the various components already discussed. A "therapeutic agent" refers to a physiologically or pharmacologically active substance that produces a localized or systemic therapeutic effect or effects in animals and refers generally to drugs, nutritional supplements, vitamins, minerals, enzymes, hormones, proteins, polypeptides, antigens and other therapeutically useful compounds. The dietary formulation may also further comprise a diagnostic agent.

The formulations in accordance with the present invention can be prepared by any number of conventional techniques known to those skilled in the art. For example, the core lipid, trans-palmitoleate, is first mixed with the emulsifier and the antioxidant, if one is being used. The emulsion is then prepared by slowly adding this oil phase into water with constant agitation. If an osmolality modifier is being used, it is added to the water prior to mixture with the oil phase. The pH can be adjusted at this stage, if necessary, and the final volume adjusted with water, if required.

In still another aspect of the invention, a method of treating/preventing a metabolic disease or disorder in a subject is provided, comprising administering to the subject a formulation in a form suitable for parenteral or enteral administration, that comprises palmitoleate, wherein the palmitoleate is substantially trans-palmitoleate.

In still another aspect of the invention, a method of improving the glucose metabolism in a subject with insulin resistance is provided. The method comprises administering to said subject a pharmaceutical formulation, a dietary formulation, or form of food suitable for oral administration, that comprises palmitoleate, wherein the palmitoleate is substantially trans-palmitoleate.

In yet another aspect of the invention, a method of reducing the level of an inflammatory biomarker in a subject, which marker indicates an inflammatory condition, is provided. The method comprises administering to the subject a pharmaceutical or dietary formulation, wherein the formulation is administered in an amount sufficient to reduce the level the inflammatory biomarker. The formulations comprises palmitoleate, wherein the palmitoleate is substantially trans-palmitoleate. The formulation can be in the form of an oil emulsion, or in the form of food oil suitable for oral administration.

As used herein, the terms "treating," "treatment", and "to treat" are used to indicate the production of beneficial or desired results, such as to alleviate symptoms, or eliminate the causation of a disease or disorder either on a temporary or a permanent basis, slow the appearance of symptoms and/or progression of the disorder, or prevent progression of disease. For methods of prevention, a subject to be administered the trans-palmitoleate formulation is generally a subject at risk for an inflammatory condition due to genetic predisposition, diet, exposure to disorder-causing agents, exposure to pathogenic agents, and the like. The term "treat" or "treatment" refer to both therapeutic treatment and prophylactic or preventative measures, wherein the object is to prevent or slow down the development or spread of disease or symptoms. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total). "Treatment" can also refer to prolonging survival as compared to expected survival if not receiving treatment.

The term "subject", "individual", and "patient" are used interchangeably herein, and refer to an animal, especially a mammal, for example a human, to whom treatment with a composition comprising trans-palmitoleate, as described herein, is provided.

The trans-palmitoleate formulations of the invention are to be administered over an effective regimen. As the term is used herein, the term "regimen" is used to refer to the systematic plan of administration of the formulation. As such, the regimen includes the dose per specific administration, the time course of each administration, the time period between individual administrations, the time period over which a specific dose is used, and coordination of other therapies or medications or procedures. Dosage may beneficially be adjusted over time. The individual can be monitored over the course of the regimen to track, e.g., glucose metabolism or fatty acid levels, and the dosage can be adjusted accordingly.

An "effective amount" is an amount sufficient to produce beneficial or desired results in a subject. An effective amount can be administered in one or more administrations according to a regimen. For purposes of this invention, an effective regimen is a course of administration of an effective amount of the trans-palmitoleate formulation or supplement sufficient to ameliorate, stabilize, reverse, slow or delay the progression or onset of a disease or disorder, e.g., fatty liver disease, essential fatty acid deficiency, obesity, diabetes, cardiovascular disease, or inflammatory disorder. The beneficial or desired results can be measured by monitoring the reduction in or disappearance of one or more symptoms of the disease or disorder, and/or monitoring the amount of trans-palmitoleate in the blood of the subject. One of skill in the art will recognize that an effective amount does not require complete recovery or complete prevention of a symptom, but merely a significant, sustainable, measurable reduction. For example, one or more symptoms are reduced by at least about 30%. In one embodiment, one or more symptoms are reduced by at least about 50%. In one embodiment, one or more symptoms are reduced by at least about 70%, at least about 80%, or at least about 90% measurable reduction in a symptom.

For treatment of diseases and disorders, e.g., diabetes, any form of administration known in the art may be used. When the formulation is in the form of a dietary supplement (food oil) suitable for oral administration, the formulation may provide about 5% to 60% of total energy expenditure of the subject in terms of calories. The administration may be continued for a length of time as determined by consultation with a nutritional or health advisor.

The present invention additionally provides for kits containing the trans-palmitoleate formulations for administration to a subject. The kit would provide an appropriate dosing regimen for a prescribed period. The kits of the invention comprise one or more packages or containers containing the trans-palmitoleate formulation in combination with a set of instructions, generally written instructions, relating to the use and dosage of the formulation. The packages containing the formulation may be in the form of unit doses or pharmacy bulk packages. The doses may be packaged in a format such that each dose is associated, for example, with a day of the week. There may also be associated with the kit a notice in the form prescribed by a governmental agency regulating the manufacture, use or sale of such products, which notice reflects approval by the agency of manufacture, use or sale for human or animal administration.

The present invention also provides for methods for monitoring trans-palmitoleate administration in a subject. An initial baseline amount of trans-palmitoleate in the subjects serum is determined, then trans-palmitoleate is administered to the subject as described herein, and subsequent measurements of serum trans-palmitoleate are determined and compared. For example, if the initial baseline amount of trans-palmitoleate is determined to fall within a quintile correlated with higher risk of inflammatory disease, such as a baseline of less than about 0.16% of total fatty acids, then trans-palmitoleate is administered and the subject is monitored for an increase in blood trans-palmitoleate. As another example, if the initial baseline amount of trans-palmitoleate is determined to fall within a quintile correlated with higher risk of insulin resistance, such as a baseline of less than about 0.18% of total fatty acids, then trans-palmitoleate is administered and the subject is monitored to determine an increase in blood trans-palmitoleate. The monitoring can by utilized in the treatment of dyslipidemia, inflammation, and/or metabolic disease, as described herein. The monitoring can be achieved, in part, using a computer system comprising a processor and a non-transitory program storage device readable by the computer system.

Thus embodiments of the invention also provide for systems (and computer readable medium for causing computer systems) to perform a method for determining whether an individual has dyslipidemia-mediated metabolic or inflammatory disease or a pre-disposition for a dyslipidemia-mediated metabolic or inflammatory disease based on the amount of trans-palmitoleate in the individual's blood.

A computer system suitable for use in monitoring trans-palmitoleate in a biological sample, e.g., a serum sample, can include a determination module configured to receive a biological sample and to determine the amount of trans-palmitoleate in the sample, a storage device configured to store the trans-palmitoleate analysis from the determination module, a comparison module adapted to compare the trans-palmitoleate amounts stored on the storage device with reference data, and to provide a comparison result, wherein the comparison result is indicative of relative metabolic health; and a display module for displaying a content based in part on the comparison result for the user, wherein the content is a signal indicative of relative metabolic health.

EXAMPLES

Example 1

Design and Population

CHS design and recruitment have been described. Fried et al., 1 Ann. Epidemiol. 263 (1991). Briefly, 5,201 ambulatory, non-institutionalized adults age ≥65 were selected randomly and then enrolled in 1989 to 1990 from Medicare eligibility lists in 4 U.S. communities (Forsyth County, N.C.; Sacramento County, Calif.; Washington County, Md.; Allegheny County, Pa.); an additional 687 black participants were recruited similarly and enrolled in 1992. Among all eligible adults contacted, 57% agreed to enroll. Baseline in-clinic evaluations included standardized physical examination, diagnostic testing, laboratory evaluation, and questionnaires on health status, medical history, and cardiovascular and lifestyle risk factors. Each center's institutional review committee approved the study; all participants provided informed written consent.

For independent validation, we evaluated the association of trans-palmitoleate measured in erythrocyte membranes and plasma (Sun et al., 88 Am. J. Clin. Nutr, 216 (2008)), with metabolic risk factors in a cohort of 327 generally healthy women, age=60.4±6.1 years, in the Nurses' Health Study (NHS). Relationships were evaluated for HDL-C, total:HDL-C, interleukin-6, CRP, and hemoglobinA1c. Because many samples were nonfasting, triglycerides and LDL-C were not evaluated; the number of subjects was too small to evaluate incident diabetes. Multivariable models were adjusted for age, smoking, physical activity, alcohol intake, family history, hypertension, hormone use, fasting status, and dietary carbohydrate, protein, polyunsaturated fats, saturated fat, dietary fiber, and total energy. We also evaluated correlations of trans-palmitoleate levels in plasma vs. erythrocytes in NHS (Spearman correlation[r]=0.74); and in phospholipids vs. triglycerides in CHS (n=104; r=0.54).

Example 2

Fatty Acid Measurements

Plasma phospholipid fatty acids were measured in 3,736 individuals using 1992 blood samples, considered to be the baseline for all present analyses. This included 3,238 participants randomly selected from individuals with available blood samples in 1992 and an additional 498 participants from a prior case-control study of myocardial infarction. All analyses accounted for this within-cohort sampling using inverse-probability-of-sampling weights. Plasma phospholipids were selected as an excellent marker of longer-term (4-8 week) circulating fatty acids, with similar responses as levels in erythrocyte membranes. Blood was drawn after a 12-hr fast, stored (−70° C.), and shipped on dry ice for long-term centralized storage (−80° C.). Under these conditions plasma phospholipid fatty acids are stable long-term, and in prior studies we observed no degradation, lipolysis, or oxidation after 10 years storage. Measurements were performed at the Fred Hutchinson Cancer Research Center, providing quantitative measurement of 45 fatty acids as percent of total fatty acids. Total lipids were extracted from plasma using methods of Folch, and phospholipids separated from neutral lipids by one-dimensional TLC. Fatty-acid-methyl-ester (FAME) samples were prepared by direct transesterification using methods of Lepage and separated using gas chromatography (Agilent5890 gas-chromatograph-FID-detector; Supelco fused-silica 100 m capillary column SP-2560; initial 160° C. 16 min, ramp 3.0° C./min to 240° C., hold 15 min). Identification, precision, and accuracy were continuously evaluated using model mixtures of known FAMEs and established in-house controls, with identification confirmed by GC-MS at USDA (Peoria, Ill.) or for trans-fats by silver-ion TLC. CVs were 2.5% for trans-palmitoleate and <3% for most fatty acids.

Example 3

Metabolic Outcomes, Covariates

At study-clinic examinations, risk factors were measured by trained personnel. Fried et al., 1991. Anthropometric measures including weight, height, and waist circumference were collected using standard procedures and used to calculate body mass index (BMI). Fasting total cholesterol, HDL-C, and triglycerides were measured according to CDC methods. LDL-C was calculated according to Friedewald equation, excluding individuals with hypertriglyceridemia. Fasting glucose and insulin were measured (Ektacham 700 Analyzer, Eastman Kodak Corp), and Homeostasis Assessment Model of insulin resistance (HOMA-IR) calculated as [(glucose mg/dl×insulin mU/L)/405]. Fibrinogen was measured using standard methods and C-reactive protein (CRP) using validated in-house high-sensitivity enzyme-linked-immunosorbent-assay. Seated blood pressure (BP) was measured using an appropriately-sized cuff and Hawksley random-zero-sphygmomanometer (model7076; Hawksley and Sons Limited, Sussex, England). Systolic and diastolic BPs were based on 2 averaged readings ≥30 seconds apart after a 5-minute rest. Prevalent coronary heart disease was adjudicated based on validated physician-diagnosed myocardial infarction, history of coronary revascularization, or angina. Usual frequency and types of alcoholic beverages (wine, beer, liquor) consumed were assessed. Leisure-time activity (kcal/wk) was assessed using a modified Minnesota Leisure-Time Activities questionnaire, evaluating frequency and duration of 15 different activities during the prior 2 weeks. Dietary habits were assessed in 1989-90 (3 years before the baseline blood draw in the present analysis) using a picture-sort food frequency questionnaire validated against six detailed 24-hour diet recalls spaced ~1 month apart and against plasma phospholipid fatty acids.

Example 4

Assessment of Incident Diabetes

Participants were followed by means of annual examinations for 10 years with interim and subsequent 6-month telephone contacts. Ives et al., 5 Ann. Epidemiol. 278 (1995). At each visit, detailed medication information was obtained using medication inventories. At baseline, study interviewers visited participants in their homes and asked to see all prescription medications they had taken in the previous 2 weeks. At follow-up exams, participants brought to clinic all prescription medications taken in the previous 2 weeks. Drug names, doses, and frequencies were coded according to prescription medication Medispan files. Prevalent diabetes at baseline was defined by use of insulin or hypoglycemic medication, fasting glucose ≥126 mg/dl, or nonfasting glucose ≥200 mg/dl. Incident diabetes was defined by new use of insulin or hypoglycemic medication (assessed annually), fasting glucose ≥126 mg/dl (assessed in 1992 and 1996), or 2-hr postchallenge glucose≥200 mg/dl (assessed in 1996).

Statistical Analysis:

Relationships between phospholipid fatty acids were evaluated using Spearman correlation. Trans-palmitoleate levels were evaluated in sex-specific quintiles as indicator variables and continuously per SD difference. Independent demographic and lifestyle determinants of trans-palmitoleate were evaluated using multivariable-adjusted linear regression with trans-palmitoleate as the dependent variable. Multivariable-adjusted relationships of trans-palmitoleate with metabolic risk factors (transformed for normality as appropriate) were evaluated using linear regression with trans-palmitoleate as the independent variable. Quintiles were evaluated as ordinal variables to assess trend, to assess effect modification using the Wald test for a multiplicative interaction term, and to assess differences in baseline characteristics by means of linear or logistic regression. Cox proportional-hazards were used to estimate the hazard ratio (hereafter relative risk, RR) of incident diabetes, with time at-risk until first diagnosis, last follow-up visit with medication information, or administrative censoring in 2006, the latest date of adjudicated medication data. Medication information was complete for 96.4% of person-time; follow-up for vital status was 100% complete. The proportional-hazards assumption was not rejected based on Schoenfeld residuals. To minimize potential confounding, covariates were selected based on biologic interest, being well-established risk factors for metabolic risk, or associations with exposures/outcomes in the present cohort. Missing covariates (most factors≤1.9%; dietary factors=7-10%) were imputed by best-subset regression using age, sex, race, education, prevalent CHD, stroke, diabetes, smoking status, alcohol use, physical activity, BMI, and, for nutritional factors, other relevant dietary variables; results excluding missing values were similar. Analyses were performed using Stata10.1 (College Station, Tex.), two-tailed alpha=0.05.

Example 5

Trans-Palmitoleate Effects Positive Glucose Uptake

C2C12 myoblasts were maintained in 20% fetal bovine serum. To differentiate the myoblasts, cells were plated in 12-well plates coated with 0.2% gelatin and medium changed to 2% horse serum upon confluence. Five days post-differentiation, C2C12 myotubes were incubated in serum-free medium with 0.5% bovine serum albumin (Sigma) and indicated fatty acids at a final concentration of 0.25 mM for 6 hr. Glucose uptake assay was performed as described previously, with modifications. Somwar et al., 276 J. Biol. Chem. 46079 (2001). Briefly, cells were washed twice with 500 μl warm Krebs-Ringer-Hepes (KRH) buffer and 1 ml of KRH buffer was added into each wells. $^3$H 2-D-Glucose (0.5 μCi/well) was added and cells were kept in incubator for 10 min. Medium was then removed and cells washed twice with ice-cold KRH buffer. Cells were plated on ice and lysed in 500 μl 0.1% SDS. Aliquots of 400 μl cell lysate were used for scintillation counting and protein assay quantification assay was performed on the rest of cell lysate. The uptake was normalized to protein concentration and expressed as percentage to the controls, shown in FIG. 1.

Example 6

Bioavailability of Trans-Palmitoleate Administered Orally

Figure 3:
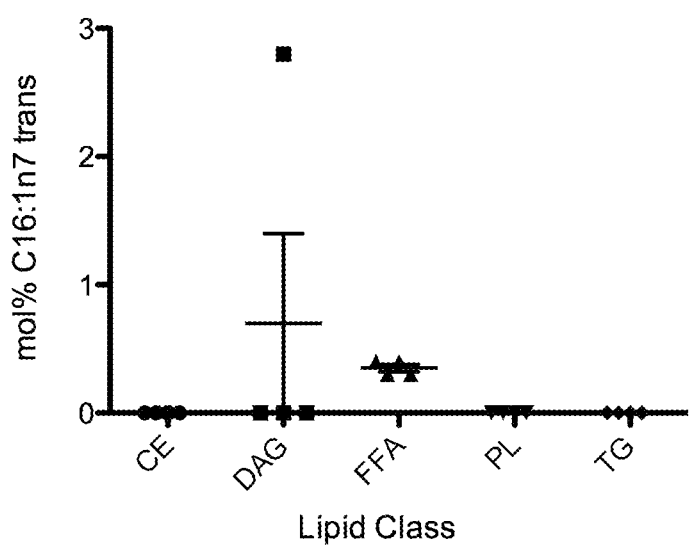
FIG. 3 is a bar graph showing the mol % plasma trans-palmitoleate per lipid class: cholesterol ester (CE); diacylglycerol (DAG); free fatty acid (FFA); phospholipid (PL); and triglyceride (TG).

Trans-palmitoleate was obtained in pure, powdered form from Nu-Check Prep, Inc. (Elysian, Minn.) and dissolved in a polyethylene glycol vehicle (PEG 300). Mice were administered, by gavage, trans-palmitoleate in doses ranging from 200 mg/kg/day to 2 g/kg/day for 5 weeks. High doses were well-tolerated, with no ill effects observed in OB/OB, wild-type, and high-fat diet mice. In OB/OB mice, after 2 weeks of treatment, plasma lipid analysis was determined from samples taken after 6 hr of fasting, 30 hr after last trans-palmiloleate administration. The mol % plasma trans palmitoleate per lipid class is shown in FIG. 3. Additionally, research diets comprising mouse chow at 2% trans-palmitoleate % total food weight can be formulated.

Figure 2:
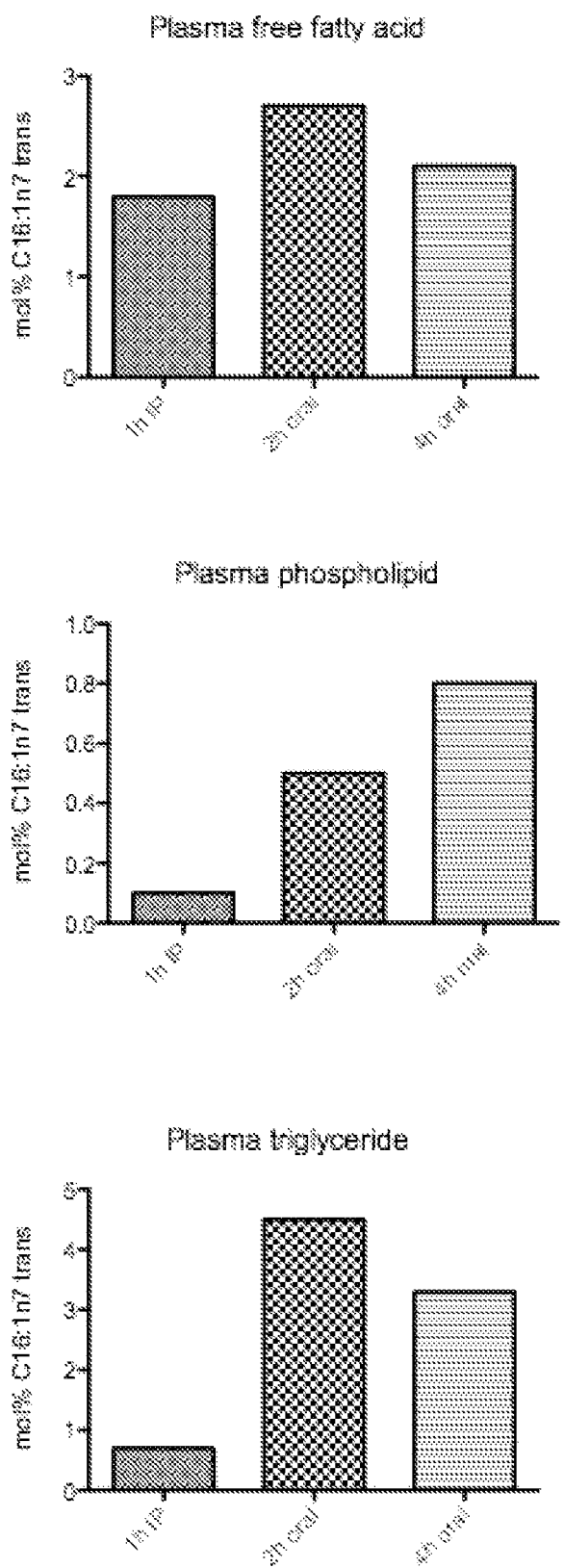
FIG. 2 is a series of bar graphs showing the bioavailability of trans-palmitoleate following oral administration (gavage) in a mouse model.

In a comparison study, trans-palmitoleate (400 mg/kg in PEG vehicle) was administered to wild-type mice by intraperitoneal injection, and serum collected 1 hr later, or the same amount was administered via gavage and serum collected at 2 hr and 4 hr later. As shown in FIG. 2, Trans-palmitoleate was detected in serum sampled after administration by both methods, supporting conclusion that oral consumption of trans-palmitoleate provides for bioavailable, circulating trans-palmitoleate.

We claim:

1. A method of treating diabetes mellitus, insulin resistance, or atherogenic dyslipidemia in a subject comprising administering to the subject a pharmaceutical, nutraceutical or dietary formulation, or dietary supplement, comprising trans-palmitoleate, wherein trans-palmitoleate is at least 6% of total fatty acids present in the formulation.

* * * * *

UNITED STATES PATENT AND TRADEMARK OFFICE
CERTIFICATE OF CORRECTION

PATENT NO. : 8,889,739 B2  
APPLICATION NO. : 13/809181  
DATED : November 18, 2014  
INVENTOR(S) : Mozaffarian et al.

Page 1 of 1

It is certified that error appears in the above-identified patent and that said Letters Patent is hereby corrected as shown below:

In the Specification

At Column 1, under the heading GOVERNMENT SUPPORT:
"This invention was made with government support under grants RO1-HL085710, DK064360, DK71507-04, awarded by the National Institutes of Health. The U.S. government has certain rights in the invention."

Should be replaced with:
—This invention was made with government support under DK064360, DK07150, and HL085710 awarded by the National Institutes of Health. The government has certain rights in the invention.—

Signed and Sealed this  
Twelfth Day of May, 2020

Andrei Iancu  
*Director of the United States Patent and Trademark Office*